United States Patent [19]

Stapp

[11] 4,221,916
[45] Sep. 9, 1980

[54] OXIDATIVE ESTERIFICATION PROCESS

[75] Inventor: Paul R. Stapp, Bartlesville, Okla.

[73] Assignee: Phillips Petroleum Company, Bartlesville, Okla.

[21] Appl. No.: 936,952

[22] Filed: Aug. 25, 1978

[51] Int. Cl.$^2$ .............................................. C07C 67/05
[52] U.S. Cl. .............................. 560/243; 260/410.6; 260/464; 260/465 D; 260/465.4; 560/1; 560/80; 560/83; 560/84; 560/87; 560/89; 560/106; 560/112; 560/122; 560/126; 560/139; 560/145; 560/183; 560/192; 560/193; 560/197; 560/198; 560/228; 560/229; 560/230; 560/246
[58] Field of Search ............... 560/243, 246, 1, 80, 560/83, 84, 87, 89, 106, 112, 122, 126, 139, 145, 183, 192, 197, 198, 228, 229, 230; 260/410.6, 464, 465 D, 465.4

[56] References Cited

U.S. PATENT DOCUMENTS

| | | | |
|---|---|---|---|
| 3,190,912 | 6/1965 | Robinson | 560/244 |
| 3,335,174 | 8/1967 | Norton | 560/243 |
| 3,689,535 | 9/1972 | Kollar | 560/246 |
| 3,701,804 | 10/1972 | Knotl | 260/530 |
| 4,052,442 | 10/1977 | Tamura | 560/243 |
| 4,069,381 | 1/1978 | Gaenzler | 560/246 |

FOREIGN PATENT DOCUMENTS

| | | | |
|---|---|---|---|
| 1528321 | 6/1968 | France | 560/243 |
| 43-7204 | 3/1968 | Japan | 560/245 |
| 43-7205 | 3/1968 | Japan | 560/243 |
| 43-25484 | 11/1968 | Japan | 560/243 |
| 45-4964 | 2/1970 | Japan | 560/243 |
| 45-21294 | 7/1970 | Japan | 560/243 |
| 45-21489 | 7/1970 | Japan | 560/243 |
| 51-108010 | 9/1976 | Japan | 560/243 |
| 1003347 | 9/1965 | United Kingdom | 560/245 |
| 1101224 | 1/1968 | United Kingdom | 560/243 |
| 1147211 | 4/1969 | United Kingdom | 560/243 |
| 504754 | 5/1976 | U.S.S.R. | 560/243 |

*Primary Examiner*—Natalie Trousof
*Assistant Examiner*—Michael Shippen

[57] ABSTRACT

Saturated vicinal esters produced by reacting olefins with carboxylic acid and anhydrides thereof in the presence of oxygen and a vanadium- or ruthenium-containing catalyst.

5 Claims, No Drawings

OXIDATIVE ESTERIFICATION PROCESS

This invention relates to a process for the oxidative esterification of olefins. In accordance with another aspect, this invention relates to the process for the oxidative esterification of olefins in the presence of vanadium- or ruthenium-containing catalysts. In accordance with a further aspect, this invention relates to a process for the conversion of olefinic carbon-carbon double bonds to vicinal diester groups by reaction with a carboxylic acid or carboxylic acid anhydride or mixture thereof in the presence of oxygen and a vanadium- or ruthenium-containing catalyst. In accordance with one specific aspect 2-butene is converted to 2,3-diacetoxybutane by reaction with a carboxylic acid or anhydride thereof in the presence of oxygen and a vanadium- or ruthenium-containing catalyst.

Accordingly, an object of this invention is to provide an improved process for the oxidative esterification of olefins.

A further object of this invention is to provide a catalyst suitable for oxidative esterification reaction.

Other objects, aspects, as well as the several advantages of the invention will be apparent to those skilled in the art upon reading the specification and the appended claims.

In accordance with the invention, a process is provided for the production of saturated vicinal esters which comprises reacting an olefinic compound with a carboxylic acid or anhydride thereof in the presence of free oxygen and a catalytically effective amount of vanadium- or ruthenium-containing catalysts.

One specific embodiment of the invention trans-2-butene is converted to 2,3-diacetoxybutane by reaction with a carboxylic acid or anhydride thereof in the presence of oxygen and a vanadium-containing or ruthenium-containing catalyst.

I. Olefinic Reactant

The instant invention is concerned with a process and catalyst for the conversion of olefinic carbon-carbon double bonds to vicinal diester groups by oxidation of said olefinic compound in the presence of a vanadium- or ruthenium-containing catalyst and further in the presence of a carboxylic acid or carboxylic acid anhydride or mixture thereof. The above described transformation may be illustrated in a specific chemical equation as follows:

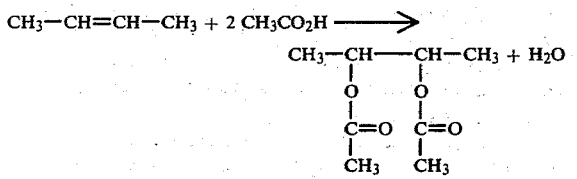

The olefinic reactant which is oxidized according to the process of the instant invention can be selected from the group consisting of acyclic olefinic compounds containing from 3 to 18 carbon atoms per molecule and having 1, 2, or 3 carbon-carbon double bonds per molecule and cyclic olefinic compounds containing from 5 to 18 carbon atoms per molecule and having 1, 2, or 3 carbon-carbon double bonds per molecule. As a further limitation, those olefinic reactants which contain 2 or 3 carbon-carbon double bonds per molecule should not have said double bonds in a conjugated relationship. Within the limitations described above, suitable olefinic reactants can be represented by the general formula RCH=CHR' wherein R and R' are selected from the group consisting of hydrogen, alkyl, alkenyl, alkadienyl, cycloalkyl, cycloalkenyl and cycloalkadienyl radicals and wherein R can be the same or different from R' and wherein R and R' taken together can form an alkylene or alkenylene or alkadienylene radical thus forming a cyclic system. It is further provided within the above limitations that R or R' when not representing hydrogen can also contain one or more oxidation resistant substituents such as carbalkoxy, carboxy, halide, cyano, nitro, and aryl groups provided that such substituents are not attached directly to a carbon-carbon double bond.

Examples of suitable monoolefinic compounds include: propylene, 1-butene, 2-butene, 1-pentene, 2-pentene, 1-hexene, 2-hexene, 3-hexene, 2-octene, 1-decene, 3-dodecene, 1-hexadecene, 1-octadecene, 9-octadecenoic acid, vinyl cyclohexane, 3-buteneitrile, cyclopentene, cyclohexene, cycloheptene, cyclooctene, cyclododecene, 3,4-dichlorocyclohexene, 3,4-dicyanocyclohexene, and the like.

Examples of suitable nonconjugated diolefinic compounds include: 1,4-hexadiene, 1,5-dexadiene, 4-vinylcyclohexene, 1,5-cyclooctadiene, 1,9-decadiene, 1,7-octadiene, 1,4-pentadiene, 9,12-octadecadienoic acid, and the like.

Examples of suitable nonconjugated triolefinic compounds include: 1,5,9-cyclododecatriene, 9,12,15-octadecatrienoic acid, and the like.

II. Carboxylic Acid Reactant

In the process of the instant invention, an olefinic reactant described above is reacted with a carboxylic acid or carboxylic acid anhydride or mixture thereof in the presence of free oxygen and a vanadium or ruthenium-containing catalyst to produce saturated vicinal esters. The carboxylic acid reactant utilized in the present invention is selected from the group consisting of monocarboxylic acids having from 2 to 18 carbon atoms per molecule described by the general formula: R''COOH, and dicarboxylic acids having form 3 to 18 carbon atoms per molecule described by the general formula: R'''(COOH)$_2$ wherein R'' is selected from the group consisting of alkyl, cycloalkyl, and aryl radicals and halogen, cyano, and -COOR'$^v$ substituted derivatives thereof, wherein up to 4 halogen, cyano, or -COOR'$^v$ substituents can be present in the R'' group; and wherein R''' is selected from the group consisting of alkylene, cycloalkylene and arylene radicals and halogen, cyano and -COOR'$^v$ substituted derivatives thereof wherein up to 4 halogen, cyano or -COOR'$^v$ substituents can be present in the R''' group. R'$^v$ is an alkyl or cycloalkyl radical having from 1 to 6 carbons.

Examples of suitable carboxylic acids include: acetic acid, propanoic acid, butanoic acid, pentanoic acid, hexanoic acid, octanoic acid, dodecanoic acid, octadecanoic acid, cyclopentanecarboxylic acid, cyclohexanecarboxylic acid, benzoic acid, chloroacetic acid, cyanoacetic acid, trichloroacetic acid, 2-bromododecanoic acid, 2-ethylhexanoic acid, succinic acid, malonic acid, adipic acid, terephthalic acid, 2-bromobutanoic acid, ethyl hydrogen adipate, 4-chlorobenzoic acid, 4-cyanobenzoic acid, 2,3,4,5-tetrachlorobenzoic acid, ethyl hydrogen-o-phthalate, and the like.

Suitable carboxylic acid anhydrides are those which correspond to the above described monocarboxylic acids, i.e.,

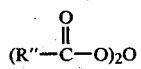

wherein R" is the same as previously defined.

The amount of carboxylic acid, carboxylic acid anhydride or mixture thereof which is utilized according to the instant invention should be at least sufficient to provide two equivalents of acycloxy moiety per equivalent of carbon-carbon double bond moiety in the olefinic reactant. Generally, it is desirable and convenient to employ an amount in excess of the above ratio to improve yields of the saturated vicinal esters. Furthermore, the excess carboxylic acid, carboxylic acid anhydride, or mixture thereof can serve effectively as a diluent for the reaction.

As described above, the reaction of the instant invention is carried out in the presence of a carboxylic acid or carboxylic acid anhydride or mixture thereof which provides the acyloxy moiety of the final product. It is presently preferred to employ as part of the reaction mixture, the corresponding carboxylic acid anhydride in addition to the carboxylic acid. The use of the carboxylic acid anhydride serves to simplify the purification and separation steps by reducing the amount of by-products which contain free hydroxyl groups. Similarly, the monocarboxylic acids are preferred over the dicarboxylic acids in order to simplify purification or separation steps in recovering the product(s). The combination of acetic acid/acetic anhydride is especially useful according to the process of the instant invention.

III. Catalyst System

The reaction according to the instant invention, wherein an olefinic reactant is converted to a saturated vicinal ester by reaction with a carboxylic acid and/or a carboxylic acid anhydride in the presence of free oxygen, is carried out in the presence of a catalyst system comprising a vanadium or a ruthenium-containing compound.

Said vanadium-containing compounds include vanadium oxides, hydroxides, acetylacetonates, carboxylates, nitrates and the like. Specific examples of suitable catalysts include vanadium oxide (VO), vanadium dioxide ($VO_2$), vanadium (III) trioxide ($V_2O_3$), vanadium pentoxide ($V_2O_5$), vanadium (IV) hydroxide, vanadyl bis(acetylacetonate) [$VO(acac)_2$], vanadyl triacetate [$VO(OAc)_3$], dioxovanadium (V) nitrate [$VO_2(NO_3)$] and the like. The presently preferred vanadium compound for the practice of this invention is vanadium pentoxide ($V_2O_5$).

Said ruthenium-containing compounds include ruthenium oxides, hydroxides, acetylacetonates, carboxylates, nitrates, and the like. Specific examples of suitable catalysts include ruthenium oxide (RuO), ruthenium dioxide ($RuO_2$), ruthenium tetraoxide ($RuO_4$), ruthenium (III) hydroxide [$Ru(OH)_3$], ruthenium (IV) hydroxide [$Ru(OH)_4$], ruthenium tris(acetylacetonate), diruthenium pentacetate, ruthenium (IV) nitrate [$Ru(NO_3)_4$] and the like. The presently preferred ruthenium compound for the practice of this invention is ruthenium dioxide ($RuO_2$).

The amount of vanadium or ruthenium-containing compound utilized as the catalyst is broadly from about 1 to about 200 millimoles per mole of olefinic reactant and preferably from about 10 to about 100 millimoles per mole of olefinic reactant.

IV. Reaction Conditions

The reaction of the instant invention is presently preferably carried out in the liquid phase with all reactants and catalysts substantially in the liquid phase with the exception, of course, of oxygen which is a reactant in the instant invention.

As noted above, the reaction of the instant invention is carried out in the presence of free oxygen. The amount of oxygen present is not believed to be critical though it is recognized that an undesirably slow reaction will result if the concentration of oxygen is very low. Essentially pure oxygen can be employed as well as mixtures of oxygen with inert gases or ambient air can be employed as a source of free oxygen for the instant reaction. It is recognized that explosive conditions could be obtained if the amount of oxygen added to the reaction system is not under control. The reaction of this invention, as is true with many oxidation reactions, appears to be highly exothermic and this too indicates caution in adding oxygen to the system. Because of these considerations, it is desirable to add the oxygen incrementally or continuously during the reaction to avoid an explosive range of oxygen concentration and to allow better control for the temperature of the reaction. A reaction vessel with efficient mixing means is also desirable to avoid build-up of dangerous concentrations of free oxygen. The reaction is carried out under an oxygen pressure which is generally from about 0.69 to about $6.9 \times 10^3$ kPa (0.1 to 1,000 psig) preferably from about 34.4 to about $1.4 \times 10^3$ kPa (5 to 200 psig) of oxygen above the autogenous pressure obtained at the temperature employed.

The temperature employed for the reaction of the instant invention is broadly from about 50°–225° C. and preferably from about 70°–150° C.

The reaction time employed in the process of this invention is not critical, and can range widely, depending generally upon the desired degree of conversion of the starting olefinic reactant. Exemplary reaction times can range between such as about 1 hour to over 20 hours in a batch process. Although not usually required, it is within the scope of this invention to utilize added inert diluents for the reaction especially when solid carboxylic acids or anhydrides are utilized as reactants. Suitable diluents which may be used include: chlorobenzene, benzene, sulfolane, methyl benzoate, and the like. It is also possible to utilize a portion of previously recovered reaction product (saturated vicinal esters) as a diluent in the reaction mixture.

The reaction according to the instant invention is generally carried out in reaction vessels of stainless steel though other materials of construction suitable for use under oxidizing conditions can also be utilized.

The reaction mixtures obtained according to the process of the instant invention can be processed by conventional methods utilizing such as fractional distillation, and the like, to recover the desired product(s) of the invention. It is possible to recover unreacted olefinic reactant and carboxylic acid reactant with recycle of the same as desired to the reaction zone. Generally, the catalyst can also be recycled to the reaction zone after removal of the unreacted starting materials and products. Thus, in a typical work-up of the reaction mixture, the catalyst system of the instant invention will usually be found in the distillation kettle residue fraction.

V. Product Utility

The saturated vicinal esters which can be obtained by reaction of the olefinic compounds with carboxylic acids and/or carboxylic acid anhydrides according to this invention have utility as solvents and plasticizers. Furthermore, the vicinal esters can be hydrolyzed to vicinal glycols or polyols depending on the number of carbon-carbon double bonds in the starting olefinic reactant. Said glycols and polyols are also useful as solvents, humectants, and the like.

VI. EXAMPLES

EXAMPLE I

A run was carried out according to the instant invention wherein a one liter stainless steel reactor equipped with heating and stirring means was charged with 300 ml (3.18 moles) acetic anhydride, 1.8 g (10 mmoles) vanadium pentoxide, and 35.0 g (625 mmoles) trans-2-butene (charged in the vapor phase). The reactor was pressured to 206.7 kPa (30 psig) with oxygen and heated to 140° C. The reaction was continued for 4.6 hours during which time at 10-30 minute intervals the pressure on the reactor was increased stepwise to a maximum $1.45 \times 10^3$ kPa (210 psig) with oxygen. After each addition of oxygen, the temperature was noted to briefly increase in the reactor by 1° to 2° which indicated the exothermic nature of the oxidation reaction taking place. At the conclusion of the reaction, the reactor was cooled, vented, opened and the contents were filtered and transferred to a distilling flask. The reaction mixture was fractionally distilled through a distillation column packed with 6 millimeter Raschig rings. Five overhead fractions were collected in the distillation. The first two fractions (total of 313 g) were collected at atmospheric pressure and contained acetic acid and lower boiling components. The remaining three overhead fractions, which were collected at reduced pressure, were analyzed by gas-liquid chromatography and were found to contain 34.6 g (199 mmoles) 2,3-diacetoxybutane. Thus, the yield of diacetate was 31.8% based on the amount of trans-2-butene charged. These results demonstrate that vanadium pentoxide successfully catalyzed the oxidation of trans-2-butene to the corresponding saturated vicinal diester in the presence of acetic anhydride.

EXAMPLE II

Another run (run no. 2) was carried out according to the instant invention which utilized the same reactor as employed in Example I. In this run, the reactor was charged with 300 ml (3.18 moles) acetic anhydride, 3.4 g (20 mmoles) ruthenium dioxide dihydrate, and 36 g (642.8 mmoles) trans-2-butene (charged in the vapor phase). The reactor was pressured to 206.7 kPa (30 psig) with oxygen and heated to 140° C. The reaction was continued for 4 hours during which time at 10-30 minute intervals the pressure on the reaction was increased stepwise to $1.17 \times 10^3$ kPa (170 psig) with oxygen. At the conclusion of the reaction, the reactor was cooled, vented, opened and the contents were filtered into a distilling flask using a small amount of fresh acetic anhydride for the transfer. The reaction product was distilled through a distillation column packed with 6 millimeter Raschig rings. Four overhead fractions were collected in the distillation and the distillation residue weighed 7.5 g. The first two fractions (total of 302.1 g) were collected at atmospheric pressure and contained acetic anhydride and lower boiling components. The remaining two fractions, which were collected at reduced pressure, were analyzed by gas-liquid chromatography and were found to contain a total of 43.0 g (247 mmoles) 2,3-diacetoxybutane. Thus, the yield of 2,3-diacetoxybutane was 38.4% based on the amount of trans-2-butene charged. This result demonstrates that ruthenium dioxide successfully catalyzed the oxidation of trans-2-butene to the corresponding saturated vicinal diester in the presence of acetic anhydride.

EXAMPLE III

A control run (run no. 3) was conducted in which selenium dioxide was used in place of the vanadium or ruthenium-containing catalyst in the system of the instant invention. To the same one liter reactor employed in run 1 of Example I above was charged 300 ml (3.18 moles) acetic anhydride, 1.1 g (10 mmoles) selenium dioxide, and 39.0 g (696 mmoles) trans-2-butene. The reactor was pressured to 206.7 kPa (30 psig) with oxygen, heated to 140° C., and then pressured stepwise to $1.03 \times 10^3$ kPa (150 psig) with oxygen. In contrast with the reaction in Example I, no temperature rise was observed with oxygen addition and no decrease in oxygen pressure was observed between oxygen additions. This indicated that the oxidation reaction of this invention was not occurring during the four hour time period. The reactor was cooled, vented, opened and the reactor contents discarded.

The result of this run demonstrates that the reaction of this invention does not occur to any significant extent in the presence of selenium dioxide, a compound outside the scope of catalysts of this invention.

EXAMPLE IV

A control run (run no. 4) was carried out in which ethylene was utilized as the olefinic reactant in the system of the instant invention. The one liter stainless steel autoclave used in Example I was charged with 300 ml (3.18 moles) acetic anhydride, 3.4 g (20 mmoles) ruthenium dioxide dihydrate, and 55 g (1.964 moles) ethylene. The reactor was heated to 120° C. and then pressured to $3.2 \times 10^3$ kPa (465 psig) and later to $5.65 \times 10^3$ kPa (820 psig) with oxygen during the 6.5 hour reaction period. After 2.5 hours the reactor temperature was increased to 140° C. The reactor was shutdown overnight and then restarted the following day with the temperature taken to 150° C. and continued for 8.8 hours. During this reaction period, the pressure was increased once to $5.58 \times 10^3$ kpa (810 psig). At the end of the reaction period, the reactor was cooled, vented, opened, and the reaction product was filtered into a distilling flask using a small amount of fresh acetic anhydride for transfer. The reaction mixture was distilled in essentially the same manner as in Example I. Essentially all of the reaction mixture distilled at 125°-145° C. at atmospheric pressure leaving no higher boiling residue, indicating that no appreciable amount of reaction had occurred. The results of this run indicate that ethylene, an olefin outside the scope of reactants of this invention, could not be converted under the conditions utilized to a saturated vicinal diester, i.e., ethylene glycol diacetate.

EXAMPLE V

Another control run was carried out in which butadiene was utilized as the olefinic reactant in the system of the instant invention. A 250 ml Fischer-Porter aerosol compatibility bottle equipped with a magnetic stirrer and heating means was charged with 100 ml (1.06 moles) acetic anhydride, 0.9 g (5 mmoles) vanadium pentoxide, and 12.2 g (225.9 mmoles) of butadiene (in vapor phase). The bottle was placed in an oil bath, pressured to 206.8 kPa (30 psig) with oxygen, and heated to 140° C. During the 7 hour reaction period the reaction was pressured to 827 kPa (120 psig) with oxygen at 10 to 30 minute intervals. The reactor was cooled, vented, and the contents weighed. A 5.0 g weight increase was observed as a result of the oxidation reaction. The reaction mixture was filtered using 16 g of fresh acetic anhydride for washing and the filtrate transferred to a distilling flask. The reaction mixture was fractionally distilled into two fractions under reduced pressure. The first fraction was primarily acetic anhydride and acetic acid. The second fraction weighed only 5.0 g and an analysis by gas-liquid chromatography indicate it to be a complex mixture of compounds. These results that under the conditions utilized, butadiene, a conjugated diolefin outside the scope of reactants of the instant invention, is not a suitable reactant for the production of vicinal diesters.

I claim:

1. In a process for the production of saturated vicinal esters which comprises reacting
   (a) at least one olefinic compound having at least 3 carbon atoms and having from 1 to 3 olefinic carbon-carbon double bonds and free of conjugated double bonds, with
   (b) at least one of mono- and dicarboxylic acids and monocarboxylic acid anhydride in an amount which is at least sufficient to provide at least 2 equivalents of acyloxy moiety per equivalent of carbon-carbon bond moiety in the olefinic reactant in the presence of
   (c) free oxygen, the improvement comprising contacting (a), (b) and (c) with
   (d) a catalytically effective amount of a catalyst consisting essentially of an oxide, hydroxide, acetylacetonate, carboxylate or nitrate of vanadium or ruthernium under conditions which produce saturated vicinal esters.

2. A process according to claim 1 wherein
   (a) is selected from acyclic olefins having from 3 to 18 carbon atoms and cyclic olefins having from 5 to 18 carbon atoms,
   (b) is selected from acids and anhydrides having from 2 to 18 carbon atoms and the amount present is at least sufficient to provide at least 2 equivalents of acyloxy moiety per equivalent of carbon-carbon bond moiety in the olefinic reactant, and
   (d) is present in an amount ranging from about 1 to about 200 millimoles per mole of olefinic reactant.

3. A process according to claim 1 wherein (d) is vanadium pentoxide or ruthenium dioxide.

4. A process according to claim 1 wherein (a) is trans-2-butene, (b) is acetic anhydride and (d) is vanadium pentoxide.

5. A process according to claim 1 wherein (a) is trans-2-butene, (b) is acetic anhydride and (d) is ruthenium dioxide.

* * * * *